United States Patent [19]

Cohen et al.

[11] Patent Number: 5,417,750
[45] Date of Patent: May 23, 1995

[54] DENTAL OR MEDICAL ALGINATE IMPRESSION MATERIAL

[75] Inventors: Brett I. Cohen, Nanuet; Barry L. Musikant, New York, both of N.Y.

[73] Assignee: Essential Dental Systems, Inc., Hackensack, N.J.

[21] Appl. No.: 249,871

[22] Filed: May 26, 1994

[51] Int. Cl.⁶ .......................... A61C 9/00; A61K 6/10
[52] U.S. Cl. ................................. 106/35; 523/109; 524/28
[58] Field of Search .................. 523/109; 524/28; 106/35, 38.4, 38.35

[56] References Cited

U.S. PATENT DOCUMENTS

| | | | |
|---|---|---|---|
| 4,543,372 | 9/1985 | Watanabe et al. | 105/35 |
| 4,836,853 | 6/1989 | Gribi | 106/35 |
| 5,244,933 | 9/1993 | Eidenbenz et al. | 106/35 |

OTHER PUBLICATIONS

Grant and Hackh's Chemical Dictionary; Grant, ed.; 5th ed.; pp. 487, 531, 529–530; 1989.

*Primary Examiner*—Karl Group
*Assistant Examiner*—C. M. Bonner
*Attorney, Agent, or Firm*—Gottlieb, Rackman, Reisman

[57] ABSTRACT

A dental or medical alginate impression composition is provided. The composition includes an alginate material comprising an alginate in an amount between about 10 and 50 weight percent, a filler material in an amount between about 10 and 90 weight percent, and a binder material in an amount between about 1 and 80 weight percent. The composition also includes a silane coating that is added to either the filler or to the alginate material as a whole.

22 Claims, No Drawings

DENTAL OR MEDICAL ALGINATE IMPRESSION MATERIAL

BACKGROUND OF THE INVENTION

This invention relates to a dental or medical impression composition, and more particularly, to an alginate impression composition that is hydrophilic.

Alginate impression materials are well known in the art and are used in both dentistry and medicine. In dentistry, alginate impression materials are used to take impressions of teeth in orthodontics, prosthodontics, and other dental practices.

In addition, alginates are particularly useful in medical procedures, such as maxillofacial reconstruction. Specifically, impressions are taken after a surgical procedure is performed, and the surgically injured tissues have healed.

In general, an alginate impression material is mixed with water and allowed to set for 2 to 15 minutes. Conventional alginate impression materials are hydrophobic, thus requiring vigorous mixing of the alginate/water mixture following the addition of water. After thorough mixing, a homogenous material is obtained, which is used to make the desired impression.

Since conventional alginate impression materials are hydrophobic, when dental impressions are taken, the applied teeth must be substantially dry. This is sometimes very difficult for the dental practitioner to achieve, resulting in imperfections associated with the dental impression.

In addition, because of the hydrophobic nature of the alginate impression material, a higher water to powder ratio has to be used. This is because a greater quantity of water is required in order to facilitate manipulation of the impression material. As a result, the alginate matrix in the material is weaker than desired. Thus, storage and use of a conventional alginate impression material are made rather difficult.

Furthermore, when water is added to the alginate powder, since the material is hydrophobic, it becomes much more difficult for the practitioner to achieve complete incorporation or absorption of the water into the material. In turn, preparation of a dental or medical impression is made difficult.

Moreover, in surgical procedures, because the eventual prosthesis is often held in by undercuts in the surgical site, it is advantageous to have an alginate impression material that is strong, flexible enough to accurately record all internal surface architecture, and with the ability to free itself from the undercut without tearing upon removal from the site. However, conventional alginate materials have been too weak to consistently offer these desirable properties.

Accordingly, it would be desirable to provide a dental or medical alginate impression composition that overcomes the above-identified disadvantages.

SUMMARY OF THE INVENTION

Generally speaking, in accordance with the invention, a dental or medical alginate impression composition is provided. The composition includes an alginate material comprising an alginate in an amount between about 10 and 50 weight percent, a filler material in an amount between about 10 and 90 weight percent, and a binder material in an amount between about 1 and 50 weight percent. The composition also includes a silane coating that is added to either the filler or to the alginate material as a whole.

The alginate is preferably potassium alginate and is used to form a matrix in the composition.

The filler material is preferably diatomaceous earth and is used to increase the strength and stiffness of the alginate composition, as well as to produce a smooth texture and to ensure a non-tacky gel surface.

The binder material is preferably calcium sulfate and is added in order to form a cross-link with the alginate matrix.

The critical feature of the inventive impression composition is the addition of a silane coating. The silane coating is placed on the surface of the alginate material and renders the alginate composition substantially hydrophilic. As a result, dental impressions do not have to be done in a dry state, a stronger matrix in the alginate composition is achieved, and mixing of the alginate composition with water is rendered far less difficult.

In accordance with the invention, either the entire alginate mixture is treated with the silane coating, or the filler ingredient is separately treated with the silane coating, depending upon the composition that the practitioner desires.

Accordingly, it is an object of this invention to provide an improved alginate impression composition which is suitable for application in the dental and medical fields.

Yet another object of the invention is to provide an improved alginate impression composition which is hydrophilic.

A further object of the invention is to provide an improved alginate impression composition which has a strong chemical matrix.

Another object of the invention is to provide an improved alginate impression composition which is easier for the medical or dental practitioner to handle.

Still other objects and advantages will in part be obvious and will in part be apparent from the following description.

The invention accordingly comprises the several steps and the relation of one or more of the steps with respect to each of the others, and the composition or compositions having the features, properties, and relation of constituents which are exemplified in the following detailed disclosure, and the scope of the invention will be indicated in the claims.

DETAILED DESCRIPTION OF THE PREFERRED EMBODIMENT

The alginate impression composition of the invention includes an alginate material comprising an alginate, a filler and a binder. The alginate ingredient is present in an amount between about 10 and 50 weight percent based on the weight of the alginate material. Preferably, the alginate is a salt alginate and is selected from either potassium alginate, magnesium alginate or sodium alginate. The purpose of the alginate in the composition is to provide a matrix to hold the filler ingredient.

The filler ingredient is selected from the group including diatomaceous earth, silicon dioxide, silica, quartz and barium glass. The preferred filler is diatomaceous earth. The function of the filler ingredient is to add strength to the overall inventive composition. Specifically, the filler enhances the stiffness of the alginate gel, produces a smooth body texture, and ensures a firm gel surface. The filler ingredient of the alginate material is present in an amount between about 10 and 90 weight percent based on the weight of the alginate material.

A binder ingredient is also part of the alginate material in an amount between about 1 and 50 weight percent. The binder is selected from the group including calcium sulfate, calcium carbonate, calcium chloride, calcium hydroxide and magnesium sulfate. The purpose of adding the binder ingredient is to form a cross-link with the alginate.

The alginate impression composition also must include a silane. The silane is selected from the group of triaminofunctional silane, gamma-methacryloxypropyltrimethoxysilane, gamma-glycidoxypropyltrimethoxysilane, gamma-aminopropyltrimethoxysilane, and N-beta-(aminoethyl)-gamma-aminopropyltrimethoxysilane.

The silane ingredient of the inventive composition is placed on the surface of the alginate material in order to render the material hydrophilic. This is achieved by either applying the silane directly to the filler material, or to the entire alginate material. If applied to the alginate material, it is done so in an amount between about 1 and 80 weight percent compared to the weight of the overall alginate composition, depending on the desired results. Preferably, if the silane is added to the alginate material, it is added in an amount between about 20 and 60 weight percent as compared to the weight of the overall alginate composition.

If, instead, the silane is added to the filler, it is preferably added in an amount between about 2 and 35 weight percent as compared to the weight of the filler plus the silane.

Optionally, one or more antimicrobial agents may be added to the inventive composition in an amount between about 1 and 10 weight percent based on the weight of the overall composition. Colorants may also be added between 0.05 and 2 weight percent based on the weight of the overall composition.

A retarder may be added to the inventive composition in an amount between about 1 and 20 weight percent based on the weight of the overall composition. The purpose of the retarder is to slow down the setting reaction of the alginate with the binder in order for the mixture to have adequate working time for manipulation by the practitioner. Examples include sodium phosphate, potassium phosphate, potassium oxalate, sodium oxalate, sodium carbonate, and potassium carbonate.

In order to better comprehend the inventive alginate impression alginate composition, the following examples are provided.

EXAMPLE 1

| Potassium alginate | 3.00 grams | (12 weight percent) |
|---|---|---|
| Diatomaceous earth | 18.50 grams | (74 weight percent) |
| Calcium sulfate | 3.00 grams | (12 weight percent) |
| Trisodium phosphate | 0.50 grams | (2 weight percent) |
| | 25.00 grams | (100 weight percent) |
| Triaminofunctional silane | 16.66 grams | (40 weight percent compared to the total weight of the alginate composition) |

In order to prepare the alginate composition, 3.00 grams of potassium alginate, 18.5 grams of diatomaceous earth, 3 grams of calcium sulfate, and 0.50 grams of trisodium phosphate were mixed together to provide a 25 gram mixture of alginate, and then placed into a screw-cap vial. Then, 16.66 grams of triaminofunctional silane were added to the alginate mixture and mixed for four hours with 44.41 grams of the catalyst n-propylamine in a cyclohexane suspension (50 ml). After four hours, the mixed materials were allowed to evaporate at room temperature. The resulting solid was then washed three times (3×100 ml) with a cyclohexane suspension to wash away any and all soluble and insoluble silane by-products, as well as the propylamine catalyst. The resulting washed alginate mixture was then placed in an oven and heated to 90° Centigrade for about four hours. The resulting saline coated alginate composition was then recovered (24.68 grams)—weight recovery was 98.72 percent.

In order to determine if the alginate composition was hydrophilic, a test sample was used by placing a drop of water thereon to determine if absorption took place. The test sample easily absorbed the water, thus illustrating the hydrophilic characteristic of the produced alginate composition.

EXAMPLE 2

| Sodium alginate | 5.00 grams | (20 weight percent) |
|---|---|---|
| Diatomaceous earth | 15.00 grams | (60 weight percent) |
| Calcium chloride | 4.00 grams | (16 weight percent) |
| Trisodium phosphate | 1.00 grams | (4 weight percent) |
| | 25.00 grams | (100 weight percent) |
| Triaminofunctional silane | 25.00 grams | (50 weight percent compared to the total weight of the alginate composition) |

Preparation of the alginate composition is achieved in the same manner as Example 1. The resulting silane coated alginate composition was recovered (24.50 grams)—weight recovery was 98 percent.

EXAMPLE 3

| Potassium alginate | 7.50 grams | (30 weight percent) |
|---|---|---|
| Silica dioxide | 10.00 grams | (40 weight percent) |
| Calcium chloride | 7.50 grams | (30 weight percent) |
| | 25.00 grams | (100 weight percent) |
| Gamma-methacryloxy-propyltrimethoxysilane | 6.25 grams | (20 weight percent compared to the total weight of the alginate composition) |

Preparation of the alginate composition is achieved in the same manner as Example 1. The resulting silane coated alginate composition was recovered (24.75 grams)—weight recovery was 99 percent.

EXAMPLE 4

| Potassium alginate | 6.25 grams | (25 weight percent) |
|---|---|---|
| Diatomaceous earth | 12.50 grams | (50 weight percent) |
| Calcium carbonate | 4.00 grams | (16 weight percent) |
| Potassium phosphate | 2.25 grams | (9 weight percent) |
| | 25.00 grams | (100 weight percent) |
| Triaminofunctional silane | 3.25 grams | (20 weight percent compared to the total weight of the filler plus silane) |

In order to prepare the filler composition, 13.0 grams of diatomaceous earth were placed into a screw-cap vial. Then, 3.25 grams of triaminofunctional silane were added to the diatomaceous earth and mixed for four hours with 8.66 grams of the catalyst n-propylamine in a cyclohexane suspension (50 ml). After four hours, the mixed materials were allowed to evaporate at room temperature. The resulting solid was then washed three times with a cyclohexane suspension (3×100 ml) to wash away any and all soluble and insoluble silane by-products, as well as the propylamine catalyst. The resulting washed mixture was then placed in an oven and heated to 90° Centigrade for about four hours. The resulting saline coated filler was then recovered (12.5 grams)—96.15 percent recovery. To the recovered filler was added 6.25 grams of potassium alginate, 4 grams of calcium carbonate and 2.25 grams of potassium phosphate which was mixed in order to prepare an alginate impression material composition.

In order to determine if the alginate composition was hydrophilic, a test sample was used by placing a drop of water thereon to determine if absorption took place. The test sample easily absorbed the water, thus illustrating the hydrophilic characteristic of the produced alginate composition.

EXAMPLE 5

| Magnesium alginate | 6.00 grams | (24 weight percent) |
|---|---|---|
| Silica | 15.50 grams | (62 weight percent) |
| Calcium sulfate | 3.50 grams | (14 weight percent) |
| | 25.00 grams | (100 weight percent) |
| Gamma-glycidoxypropyl-trimethoxysilane | 1.72 grams | (10 weight percent compared to the total weight of filler plus silane) |

Preparation of the alginate composition is achieved in the same manner as Example 4. 16.00 grams of filler (silica) was used at the start. The resulting silane coated alginate composition was removed (15.5 grams)—weight recovery was 96.88 percent.

In order to better appreciate the inventive alginate impression composition, a dimensional stability study of four different alginate impression materials, with five different storage procedures, was conducted.

Dimensional accuracy is one of the most important characteristics for a dental impression material. Most acceptable limits for accuracy are from 0.1% to 0.27%.

The study was divided into four groups. Group 1 was the impression composition JELTRATE, manufactured by Dentsply of Milford, Delaware, in a volume ratio of 2:2 (powder/water). Group 2 was HYDROGUM, manufactured by Zhermack of Italy, and in the volume ratio of 2:2 (powder/water). Group 3 was the inventive alginate impression composition of Example 1 in a volume ratio of 2:1.5 (powder/water); and Group 4 was the inventive alginate impression composition of Example 1 in the volume ratio of 2:2 (powder/water).

A master cast was fabricated of an acrylic resin due to its low water absorption and low thermal conductivity. The acrylic mandibular arch of a standard, Dentoform was used as a reference master cast. Reference grooves were created on the mandibular arch as reference points. This included the buccolingual on the distobuccal cusp of the left second molar and buccolingually on the buccal cusp tip of the left first premolar. Reference groups were also created mesiodistally on the distolingual cusp of the left and right first molars. In addition, diagonal measurements were measured form the left first premolar to the distobuccal cusp of the right second molar.

With respect to Groups 1 and 2, these materials were mixed in accordance with the instructions provided by the manufacturer. Specifically, the Group 1 composition comprised 20.5 grams of powder and 40 grams of water. The Group 2 composition comprised 20 grams of powder and 33.5 grams of water.

The inventive composition of Group 3 comprised 20.5 grams of powder and 30.5 grams of water. The inventive composition of Group 4 comprised 20.5 grams of powder and 40.0 grams of water.

Each alginate composition was then placed on a standard impression tray. The impression tray was placed over the acrylic master cast and hand pressure was slowly applied for about 30 seconds in order to ensure a proper fit. A 2.5 pound weight was then placed on the back position of the impression tray. All mixtures were performed at room temperatures in a stock water solution which was also stored at room temperature.

The alginate material and impression tray were carefully removed from the master cast and a quick observation was made of the resulting impression to check for any defaults. In the study, a total of 169 casts were fabricated. Each alginate material of the four groups was then subjected to five different procedures as follows:

1. Immediate pour following removal from the master cast.
2. Ten-minute storage in a wet paper towel.
3. One hour storage in a wet paper towel.
4. 24 hours in a wet paper towel.
5. 30 minute storage on a counter top without a wet paper towel.

A sample size for each of the above identified procedures consisted of at least eight of each of the groups.

After the above procedures were completed, dental stone was mixed in a volume ratio of 2:1 (powder/water) according to manufacturer's specifications. The resulting stone mixture was then vibrated into the alginate impression. The stone casts were allowed to set for about 45 minutes before removal and left to dry for 24 hours before any statistical measurements were taken, in accordance with standard statistical practice. Then measurements for buccolingual, mesiodistal and diagonal were taken. The following four tables set forth the results.

TABLE 1

| Sample # | Measurements for Jeltrate (group 1) | | |
|---|---|---|---|
| | Buccolingual | Mesiodistal | Diagonal |
| | Immediate | | |
| 1 | 36.37 ± 0.05 | 27.08 ± 0.033 | 44.03 ± 0.079 |
| 2 | 36.29 ± 0.096 | 26.94 ± 0.041 | 44.11 ± 0.041 |
| 3 | 35.94 ± 0.145 | 27.08 ± 0.049 | 44.19 ± 0.046 |
| 4 | 36.29 ± 0.036 | 27.08 ± 0.041 | 44.42 ± 0.108 |
| 5 | 36.66 ± 0.069 | 26.92 ± 0.069 | 44.44 ± 0.075 |
| 6 | 36.46 ± 0.086 | 27.41 ± 0.064 | 44.26 ± 0.027 |
| 7 | 36.36 ± 0.098 | 27.19 ± 0.031 | 44.25 ± 0.129 |
| 8 | 36.02 ± 0.041 | 27.18 ± 0.076 | 43.70 ± 0.106 |
| 9 | 36.29 ± 0.036 | 27.08 ± 0.041 | 44.42 ± 0.109 |
| 10 | 35.88 ± 0.092 | 27.01 ± 0.081 | 44.01 ± 0.119 |
| | 10 minutes with a wet towel | | |
| 1 | 35.70 ± 0.204 | 27.06 ± 0.048 | 43.61 ± 0.055 |
| 2 | 36.74 ± 0.113 | 26.91 ± 0.029 | 44.50 ± 0.04 |
| 3 | 35.65 ± 0.035 | 26.95 ± 0.025 | 43.67 ± 0.049 |
| 4 | 36.00 ± 0.166 | 27.12 ± 0.076 | 44.14 ± 0.172 |
| 5 | 36.56 ± 0.129 | 26.76 ± 0.057 | 44.11 ± 0.037 |
| 6 | 36.50 ± 0.041 | 27.15 ± 0.067 | 44.26 ± 0.047 |
| 7 | 35.81 ± 0.101 | 27.05 ± 0.037 | 44.03 ± 0.075 |
| 8 | 35.68 ± 0.04 | 27.09 ± 0.029 | 44.26 ± 0.039 |
| | 30 minutes with no wet towel | | |
| 1 | 36.48 ± 0.05 | 26.99 ± 0.074 | 44.28 ± 0.094 |
| 2 | 36.27 ± 0.05 | 26.99 ± 0.036 | 43.84 ± 0.315 |
| 3 | 36.12 ± 0.21 | 27.20 ± 0.024 | 44.60 ± 0.046 |

TABLE 1-continued

Measurements for Jeltrate (group 1)

| Sample+ | Buccolingual | Mesiodistal | Diagonal |
|---|---|---|---|
| 4 | 36.60 ± 0.097 | 27.17 ± 0.033 | 44.38 ± 0.048 |
| 5 | 35.60 ± 0.14 | 26.44 ± 0.125 | 43.78 ± 0.102 |
| 6 | 35.71 ± 0.116 | 27.04 ± 0.048 | 44.10 ± 0.12 |
| 7 | 35.89 ± 0.128 | 26.95 ± 0.05 | 44.00 ± 0.064 |
| 8 | 35.58 ± 0.15 | 27.11 ± 0.051 | 43.93 ± 0.072 |
| \multicolumn{4}{c}{1 hour with a wet towel} | | | |
| 1 | 36.33 ± 0.131 | 26.96 ± 0.033 | 43.90 ± 0.08 |
| 2 | 36.73 ± 0.071 | 27.03 ± 0.016 | 44.49 ± 0.12 |
| 3 | 37.34 ± 0.047 | 26.99 ± 0.023 | 44.25 ± 0.256 |
| 4 | 35.50 ± 0.154 | 27.18 ± 0.042 | 43.80 ± 0.018 |
| 5 | 35.72 ± 0.075 | 27.37 ± 0.073 | 44.13 ± 0.104 |
| 6 | 36.05 ± 0.045 | 26.93 ± 0.094 | 43.80 ± 0.159 |
| 7 | 35.47 ± 0.039 | 27.07 ± 0.026 | 43.71 ± 0.061 |
| 8 | 36.01 ± 0.047 | 27.09 ± 0.047 | 44.32 ± 0.096 |
| \multicolumn{4}{c}{24 hours with a wet towel} | | | |
| 1 | 35.33 ± 0.084 | 27.03 ± 0.067 | 43.30 ± 0.096 |
| 2 | 35.72 ± 0.094 | 26.82 ± 0.048 | 43.56 ± 0.067 |
| 3 | 35.76 ± 0.064 | 22.08 ± 0.027 | 43.55 ± 0.043 |
| 4 | 35.61 ± 0.014 | 27.07 ± 0.022 | 43.71 ± 0.043 |
| 5 | 35.75 ± 0.063 | 27.04 ± 0.075 | 44.03 ± 0.037 |
| 6 | 35.62 ± 0.035 | 27.07 ± 0.017 | 44.33 ± 0.12 |
| 7 | 35.44 ± 0.089 | 26.94 ± 0.051 | 43.75 ± 0.107 |
| 8 | 35.50 ± 0.054 | 26.75 ± 0.028 | 44.17 ± 0.191 |

Note: + number of observation were 10.

TABLE 2

Measurements for Hydrogum (group 2)

| Sample+ | Buccolingual | Mesiodistal | Diagonal |
|---|---|---|---|
| \multicolumn{4}{c}{Immediate} | | | |
| 1 | 37.75 ± 0.448 | 27.07 ± 0.022 | 43.61 ± 0.017 |
| 2 | 35.25 ± 0.092 | 27.07 ± 0.039 | 43.72 ± 0.151 |
| 3 | 35.77 ± 0.029 | 27.09 ± 0.039 | 43.80 ± 0.077 |
| 4 | 36.45 ± 0.093 | 27.07 ± 0.039 | 44.45 ± 0.078 |
| 5 | 36.13 ± 0.206 | 26.90 ± 0.036 | 44.17 ± 0.068 |
| 6 | 35.65 ± 0.072 | 27.05 ± 0.026 | 43.64 ± 0.074 |
| 7 | 36.41 ± 0.049 | 27.05 ± 0.028 | 44.26 ± 0.06 |
| 8 | 36.15 ± 0.055 | 26.90 ± 0.036 | 43.96 ± 9.14 |
| \multicolumn{4}{c}{10 minutes with a wet towel} | | | |
| 1 | 36.58 ± 0.113 | 26.88 ± 0.078 | 43.90 ± 0.046 |
| 2 | 35.96 ± 0.107 | 27.06 ± 0.028 | 44.14 ± 0.036 |
| 3 | 36.22 ± 0.215 | 27.05 ± 0.035 | 44.21 ± 0.068 |
| 4 | 36.23 ± 0.242 | 27.06 ± 0.054 | 44.11 ± 0.017 |
| 5 | 35.72 ± 0.029 | 26.95 ± 0.033 | 43.88 ± 0.076 |
| 6 | 36.25 ± 0.077 | 27.17 ± 0.047 | 44.10 ± 0.113 |
| 7 | 35.70 ± 0.053 | 27.23 ± 0.054 | 44.05 ± 0.081 |
| 8 | 35.62 ± 0.049 | 27.14 ± 0.032 | 43.97 ± 0.051 |
| 9 | 35.62 ± 0.123 | 27.07 ± 0.027 | 43.94 ± 0.022 |
| \multicolumn{4}{c}{30 minutes with no wet towel} | | | |
| 1 | 35.25 ± 0.093 | 27.07 ± 0.05 | 43.77 ± 0.06 |
| 2 | 35.80 ± 0.021 | 27.17 ± 0.054 | 44.01 ± 0.074 |
| 3 | 36.86 ± 0.121 | 27.06 ± 0.332 | 44.32 ± 0.095 |
| 4 | 36.30 ± 0.208 | 26.98 ± 0.067 | 44.10 ± 0.064 |
| 5 | 35.94 ± 0.061 | 26.98 ± 0.025 | 44.12 ± 0.103 |
| 6 | 35.66 ± 0.107 | 27.16 ± 0.059 | 43.60 ± 0.04 |
| 7 | 35.72 ± 0.066 | 27.08 ± 0.031 | 44.03 ± 0.06 |
| 8 | 37.01 ± 0.066 | 27.27 ± 0.074 | 44.21 ± 0.065 |
| \multicolumn{4}{c}{1 hour with a wet towel} | | | |
| 1 | 35.81 ± 0.079 | 27.06 ± 0.039 | 44.04 ± 0.119 |
| 2 | 34.40 ± 0.089 | 27.07 ± 0.033 | 43.78 ± 0.084 |
| 3 | 35.96 ± 0.101 | 27.04 ± 0.025 | 43.96 ± 0.098 |
| 4 | 36.05 ± 0.065 | 27.06 ± 0.042 | 44.05 ± 0.033 |
| 5 | 36.32 ± 0.139 | 27.05 ± 0.045 | 43.98 ± 0.047 |
| 6 | 36.25 ± 0.029 | 27.20 ± 0.035 | 43.76 ± 0.145 |
| 7 | 36.02 ± 0.029 | 26.99 ± 0.029 | 43.91 ± 0.035 |
| 8 | 36.07 ± 0.058 | 27.05 ± 0.05 | 44.01 ± 0.115 |
| \multicolumn{4}{c}{24 hours with a wet towel} | | | |
| 1 | 36.69 ± 0.136 | 27.06 ± 0.058 | 44.49 ± 0.057 |
| 2 | 35.75 ± 0.188 | 27.09 ± 0.064 | 43.72 ± 0.129 |
| 3 | 35.49 ± 0.049 | 26.82 ± 0.058 | 43.50 ± 0.077 |
| 4 | 35.35 ± 0.143 | 27.01 ± 0.088 | 44.12 ± 0.064 |
| 5 | 35.68 ± 0.103 | 27.13 ± 0.024 | 43.63 ± 0.015 |
| 6 | 36.23 ± 0.126 | 27.08 ± 0.056 | 43.91 ± 0.114 |
| 7 | 35.30 ± 0.062 | 27.08 ± 0.026 | 43.97 ± 0.13 |

TABLE 2-continued

Measurements for Hydrogum (group 2)

| Sample+ | Buccolingual | Mesiodistal | Diagonal |
|---|---|---|---|
| 8 | 35.72 ± 0.086 | 26.85 ± 0.077 | 43.77 ± 0.083 |

Note: + number of observation were 10.

TABLE 3

New Hydrophilic Alignate (group 3-power/liquid 2.1.5)

| Sample+ | Buccolingual | Mesiodistal | Diagonal |
|---|---|---|---|
| \multicolumn{4}{c}{Immediate} | | | |
| 1 | 35.80 ± 0.041 | 27.10 ± 0.04 | 43.96 ± 0.123 |
| 2 | 35.34 ± 0.034 | 27.04 ± 0.041 | 43.72 ± 0.038 |
| 3 | 35.71 ± 0.101 | 27.07 ± 0.03 | 43.83 ± 0.024 |
| 4 | 36.01 ± 0.07 | 27.01 ± 0.029 | 44.11 ± 0.04 |
| 5 | 36.52 ± 0.086 | 27.14 ± 0.037 | 44.54 ± 0.145 |
| 6 | 35.94 ± 0.139 | 27.02 ± 0.039 | 44.09 ± 0.049 |
| 7 | 36.33 ± 0.096 | 27.01 ± 0.046 | 44.67 ± 0.024 |
| 8 | 37.10 ± 0.044 | 27.32 ± 0.043 | 45.45 ± 0.153 |
| 9 | 37.02 ± 0.045 | 27.09 ± 0.067 | 44.58 ± 0.07 |
| 10 | 36.49 ± 0.054 | 27.05 ± 0.027 | 44.47 ± 0.02 |
| \multicolumn{4}{c}{10 minutes with a wet towel} | | | |
| 1 | 35.70 ± 0.221 | 27.09 ± 0.037 | 43.78 ± 0.054 |
| 2 | 35.61 ± 0.077 | 27.06 ± 0.047 | 44.40 ± 0.192 |
| 3 | 35.20 ± 0.034 | 27.07 ± 0.046 | 43.65 ± 0.084 |
| 4 | 35.23 ± 0.029 | 27.08 ± 0.034 | 43.61 ± 0.076 |
| 5 | 35.24 ± 0.053 | 27.04 ± 0.014 | 43.63 ± 0.038 |
| 6 | 35.25 ± 0.053 | 27.08 ± 0.04 | 43.61 ± 0.015 |
| 7 | 35.57 ± 0.133 | 27.05 ± 0.12 | 43.74 ± 0.118 |
| 8 | 35.92 ± 0.037 | 27.08 ± 0.032 | 43.95 ± 0.047 |
| \multicolumn{4}{c}{30 minutes with no wet towel} | | | |
| 1 | 35.61 ± 0.13 | 27.03 ± 0.075 | 43.87 ± 0.034 |
| 2 | 35.29 ± 0.067 | 27.07 ± 0.016 | 43.74 ± 0.056 |
| 3 | 35.49 ± 0.038 | 26.94 ± 0.05 | 43.64 ± 0.046 |
| 4 | 35.35 ± 0.048 | 27.07 ± 0.1 | 43.62 ± 0.032 |
| 5 | 36.89 ± 0.135 | 27.01 ± 0.021 | 45.08 ± 0.063 |
| 6 | 36.37 ± 0.118 | 27.06 ± 0.025 | 44.07 ± 0.077 |
| 7 | 35.95 ± 0.09 | 27.03 ± 0.039 | 43.91 ± 0.13 |
| 8 | 35.58 ± 0.095 | 27.19 ± 0.034 | 44.52 ± 0.04 |
| \multicolumn{4}{c}{1 hour with a wet towel} | | | |
| 1 | 35.37 ± 0.0.38 | 27.05 ± 0.054 | 43.65 ± 0.034 |
| 2 | 36.07 ± 0.077 | 27.01 ± 0.105 | 43.64 ± 0.088 |
| 3 | 35.36 ± 0.101 | 27.08 ± 0.043 | 43.69 ± 0.069 |
| 4 | 36.23 ± 0.215 | 26.81 ± 0.097 | 44.20 ± 0.065 |
| 5 | 35.71 ± 0.093 | 27.07 ± 0.027 | 43.99 ± 0.043 |
| 6 | 36.59 ± 0.079 | 26.93 ± 0.012 | 44.34 ± 0.052 |
| 7 | 35.52 ± 0.084 | 26.79 ± 0.044 | 43.73 ± 0.113 |
| 8 | 37.72 ± 0.145 | 27.36 ± 0.12 | 43.72 ± 0.084 |
| \multicolumn{4}{c}{24 hours with a wet towel} | | | |
| 1 | 35.64 ± 0.059 | 27.31 ± 0.04 | 43.66 ± 0.019 |
| 2 | 36.18 ± 0.056 | 27.18 ± 0.118 | 44.11 ± 0.135 |
| 3 | 36.64 ± 0.076 | 27.15 ± 0.099 | 44.29 ± 0.192 |
| 4 | 35.96 ± 0.111 | 27.23 ± 0.045 | 43.61 ± 0.008 |
| 5 | 36.10 ± 0.043 | 27.07 ± 0.037 | 44.14 ± 0.037 |
| 6 | 35.43 ± 0.053 | 27.41 ± 0.092 | 44.57 ± 0.071 |
| 7 | 35.71 ± 0.167 | 27.06 ± 0.033 | 44.10 ± 0.128 |
| 8 | 35.68 ± 0.052 | 27.27 ± 0.111 | 44.14 ± 0.122 |
| 9 | 35.89 ± 0.095 | 27.09 ± 0.026 | 43.82 ± 0.111 | note: + number of observation were 10.

TABLE 4

New Hydrophilic Alginate (group 4-Powder/liquid 2:2)

| Sample+ | Buccolingual | Mesiodistal | Diagonal |
|---|---|---|---|
| \multicolumn{4}{c}{Immediate} | | | |
| 1 | 35.85 ± 0.08 | 27.10 ± 0.03 | 44.10 ± 0.093 |
| 2 | 35.21 ± 0.113 | 27.07 ± 0.05 | 43.69 ± 0.042 |
| 3 | 36.52 ± 0.117 | 26.89 ± 0.084 | 44.05 ± 0.077 |
| 4 | 35.36 ± 0.088 | 26.85 ± 0.025 | 44.06 ± 0.122 |
| 5 | 35.86 ± 0.024 | 27.11 ± 0.025 | 43.89 ± 0.063 |
| 6 | 35.47 ± 0.076 | 26.99 ± 0.041 | 43.90 ± 0.036 |
| 7 | 35.89 ± 0.108 | 27.03 ± 0.062 | 44.02 ± 0.036 |
| 8 | 36.18 ± 0.078 | 27.01 ± 0.093 | 44.24 ± 0.059 |
| 9 | 36.15 ± 0.02 | 27.05 ± 0.03 | 44.11 ± 0.089 |
| \multicolumn{4}{c}{10 minutes with a wet towel} | | | |
| 1 | 35.68 ± 0.064 | 27.08 ± 0.03 | 43.72 ± 0.03 |
| 2 | 35.50 ± 0.055 | 27.02 ± 0.114 | 43.68 ± 0.064 |

TABLE 4-continued

| New Hydrophilic Alginate (group 4-Powder/liquid 2:2) | | | |
|---|---|---|---|
| Sample+ | Buccolingual | Mesiodistal | Diagonal |
| 3 | 35.41 ± 0.039 | 27.00 ± 0.03 | 43.86 ± 0.052 |
| 4 | 35.29 ± 9.137 | 27.07 ± 0.027 | 43.65 ± 0.047 |
| 5 | 35.53 ± 0.066 | 27.07 ± 0.03 | 43.82 ± 0.034 |
| 6 | 35.34 ± 0.027 | 27.04 ± 0.017 | 43.62 ± 0.086 |
| 7 | 35.51 ± 0.055 | 27.08 ± 0.024 | 43.61 ± 0.061 |
| 8 | 35.41 ± 0.128 | 27.12 ± 0.039 | 44.12 ± 0.055 |
| 9 | 35.51 ± 0.102 | 27.07 ± 0.024 | 43.70 ± 0.261 |
| 10 | 35.30 ± 0.138 | 26.80 ± 0.051 | 43.90 ± 0.098 |
| 30 minutes with no wet towel | | | |
| 1 | 35.23 ± 0.074 | 26.98 ± 0.02 | 43.85 ± 0.045 |
| 2 | 35.34 ± 0.064 | 27.03 ± 0.032 | 43.86 ± 0.031 |
| 3 | 35.19 ± 0.033 | 27.02 ± 0.019 | 43.59 ± 0.03 |
| 4 | 35.29 ± 0.101 | 27.06 ± 0.037 | 43.64 ± 0.114 |
| 5 | 35.17 ± 0.045 | 26.90 ± 0.044 | 43.57 ± 0.066 |
| 6 | 35.93 ± 0.034 | 26.94 ± 0.018 | 43.96 ± 0.113 |
| 7 | 35.22 ± 0.084 | 27.05 ± 0.039 | 43.68 ± 0.056 |
| 8 | 35.19 ± 0.009 | 26.84 ± 0.03 8 | 43.63 ± 0.08 |
| 1 hour with a wet towel | | | |
| 1 | 35.28 ± 0.063 | 27.02 ± 0.029 | 43.75 ± 0.053 |
| 2 | 35.88 ± 0.117 | 26.93 ± 0.035 | 44.37 ± 0.129 |
| 3 | 35.16 ± 0.068 | 26.54 ± 0.029 | 43.58 ± 0.121 |
| 4 | 35.53 ± 0.064 | 26.88 ± 0.039 | 43.63 ± 0.06 |
| 5 | 35.15 ± 0.035 | 26.81 ± 0.041 | 43.59 ± 0.046 |
| 6 | 35.78 ± 0.073 | 27.06 ± 0.064 | 43.97 ± 0.122 |
| 7 | 35.55 ± 0.179 | 27.05 ± 0.05 | 43.89 ± 0.154 |
| 8 | 35.91 ± 0.06 | 26.40 ± 0.029 | 44.30 ± 0.081 |
| 24 hours with a wet towel | | | |
| 1 | 35.59 ± 0.092 | 27.10 ± 0.019 | 43.82 ± 0.049 |
| 2 | 35.64 ± 0.059 | 27.08 ± 0.04 | 43.86 ± 0.116 |
| 3 | 36.13 ± 0.146 | 26.99 ± 0.063 | 44.23 ± 0.098 |
| 4 | 35.24 ± 0.077 | 27.08 ± 0.016 | 43.91 ± 0.086 |
| 5 | 35.21 ± 0.051 | 27.04 ± 0.028 | 43.68 ± 0.056 |
| 6 | 35.52 ± 0.095 | 26.97 ± 0.019 | 43.78 ± 0.057 |
| 7 | 35.63 ± 0.074 | 27.10 ± 0.03 | 43.91 ± 0.08 |
| 8 | 35.51 ± 0.053 | 26.92 ± 0.11 | 43.87 ± 0.027 | note: + number of observation were 10.

Buccolingual and diagonal measurements showed that the new Group 4 alginate composition of the invention was the only alginate that differed from the Group 1 JELTRATE composition with a smaller buccolingual and diagonal measurement. All other material studied was similar statistically with the JELTRATE composition.

The immediate method (measured buccolingually and diagonally) produced more accurate casts.

The mesiodistal data illustrated different results where none of the preparation methods differed from one another.

All other materials that were studied were similar statistically.

The inventive alginate composition of Group 3 resulted in similar dimensional accuracy as compared to JELTRATE and HYDROGUM, despite the incorporation of 25% less water.

The inventive alginate impression composition is advantageous since it does not require use in a dry condition. This is because of the hydrophilic nature of the inventive composition.

In addition, the inventive alginate impression composition has a much stronger matrix as compared to conventional alginate compositions, resulting in a tougher wear-resistent matrix.

Furthermore, the alginate impression composition of the invention is geared for the medical or dental practitioner to use. Since the composition of the invention is hydrophilic, it is simpler to mix the composition with water than prior art compositions.

It will thus be seen that the objects set forth above, among those made apparent from the preceding description, are efficiently attained, and since certain changes may be made in carrying out the above method and preparing the composition, as set forth above, without departing from the spirit and scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

We claim:

1. A dental or medical impression composition comprising:
   an alginate material comprising an alginate in an amount between about 10 and 50 weight percent, a filler in an amount between about 10 and 90 weight percent, and a binder in an amount between about 1 and 50 weight percent; and
   an organofunctional silane coating selected from the group consisting of epoxy silanes, methacrylate silanes and amino silanes, said silane coating to render the composition hydrophilic added to the alginate material in an amount between about 1 and 80 weight percent as compared to the weight of the overall alginate composition.

2. The composition of claim 1, wherein the alginate is a salt alginate.

3. The composition of claim 2, wherein the salt alginate is selected from the group consisting of potassium alginate, magnesium alginate and sodium alginate.

4. The composition of claim 3, wherein the alginate is potassium alginate.

5. The composition of claim 1, wherein the filler is selected from the group consisting of diatomaceous earth, silica, and barium glass.

6. The composition of claim 5, wherein the filler is diatomaceous earth.

7. The composition of claim 1, wherein the binder is selected from the group consisting of calcium sulfate, calcium carbonate, calcium chloride, calcium hydroxide, and magnesium sulfate.

8. The composition of claim 7, wherein the binder is calcium sulfate.

9. The composition of claim 1, wherein the silane coating is selected from the group consisting of triaminofunctional silane, gamma-methacryloxypropyltrimethoxysilane, gamma-glycidoxypropyltrimethoxysilane, gamma-aminopropyltrimethoxysilane, N-beta-(aminoethyl)-gamma-aminopropyltrimethoxysilane.

10. The composition of claim 9, wherein the silane coating is triaminofunctional silane.

11. The composition of claim 1, wherein the silane coating is added to the alginate material in an amount between about 20 and 60 weight percent as compared to the weight of the overall composition.

12. The composition of claim 1, further including at least one antimicrobial agent in an amount between about 1 and 10 weight percent, based on the weight of the overall composition.

13. The composition of claim 1, further including one or more colorants in an amount between about 0.05 and 2 weight percent, based on the weight of the overall composition.

14. The composition of claim 1, further including at least one retarder in an amount between about 1 and 20 weight percent, based on the weight of the overall composition.

15. The composition of claim 14, wherein said retarder is selected from the group consisting of sodium phosphate, potassium phosphate, potassium oxalate, sodium oxalate, sodium carbonate and potassium carbonate.

16. A method for preparing a dental or medical impression composition comprising the steps of:
   mixing an alginate in an amount between about 10 and 50 weight percent, a filler in an amount between about 10 and 90 weight percent, and a binder in an amount between about 1 and 50 weight percent in order to prepare an alginate material;
   adding an organofunctional silane coating selected from the group consisting of epoxy silanes, methacrylate silanes, and amino silanes to said alginate material following said mixing step in order to render the alginate material hydrophilic.

17. The method of claim 16, wherein said silane coating adding step comprises adding said silane coating to said alginate material after said mixing step in an amount between about 1 and 80 weight percent as compared to the weight of the overall composition.

18. The method of claim 16, wherein said silane coating adding step comprises adding said silane coating to said filler prior to said mixing step in an amount between about 2 and 35 weight percent as compared to the weight of the filler plus the silane coating.

19. A dental or medical impression composition comprising:
   an alginate material comprising an alginate in an amount between about 10 and 50 weight percent, a filler in an amount between about 10 and 90 weight percent, and a binder in an amount between about 1 and 50 weight percent; and
   a silane coating added to the alginate material in an amount between about 20 and 60 weight percent as compared to the weight of the overall alginate composition.

20. A dental or medical impression system comprising:
   an impression composition comprising:
   (1) an alginate material having an alginate in an amount between about 10 and 50 weight percent, a filler in an amount between about 10 and 90 weight percent, and a binder in an amount between about 1 and 50 weight percent; and
   (2) an organofunctional silane selected from the group consisting of epoxy silanes, methacrylate silanes and amino silanes, said silane to render the composition hydrophilic added to either the alginate material in amount between about 1 and 80 weight percent as compared to the weight of the overall alginate composition, or to the filler in an amount between about 2 and 35 weight percent as compared to the weight of the filler plus the silane coating; and
   a solvent comprising water.

21. The method of claim 16, wherein the silane coating is selected from the group consisting of triaminofunctional silane, gamma-methacryloxypropyltrimethoxysilane, gamma-glycidoxypropyltrimethoxysilane, gamma-aminopropyltrimethoxysilane, and N-beta-(aminoethyl)-gamma-aminopropyltrimethoxysilane.

22. The system of claim 20, wherein said silane is selected from the group consisting of triaminofunctional silane, gamma-methacryloxypropyltrimethoxysilane, gamma-glycidoxypropyltrimethoxysilane, gamma-aminopropyltrimethoxysilane, and N-beta-(aminoethyl)-gamma-aminopropyltrimethoxysilane.

* * * * *